United States Patent
Numata et al.

(10) Patent No.: US 7,933,441 B2
(45) Date of Patent: Apr. 26, 2011

(54) METHOD OF INSPECTION FOR INNER DEFECTS OF AN OBJECT AND APPARATUS FOR SAME

(75) Inventors: Shouhei Numata, Hitachinaka (JP); Tarou Takagi, Hitachi (JP); Noriyuki Sadaoka, Tokai (JP)

(73) Assignee: Hitachi, Ltd., Tokyo (JP)

( * ) Notice: Subject to any disclaimer, the term of this patent is extended or adjusted under 35 U.S.C. 154(b) by 1162 days.

(21) Appl. No.: 11/259,251

(22) Filed: Oct. 27, 2005

(65) Prior Publication Data

US 2006/0093082 A1 May 4, 2006

(30) Foreign Application Priority Data

Oct. 28, 2004 (JP) .................. 2004-313483

(51) Int. Cl.
*G06K 9/00* (2006.01)
(52) U.S. Cl. ............... 382/141; 700/110; 708/4
(58) Field of Classification Search .......... 382/141, 382/152, 131; 708/4; 700/110
See application file for complete search history.

(56) References Cited

U.S. PATENT DOCUMENTS

| | | | |
|---|---|---|---|
| 4,672,650 A * | 6/1987 | Masanobu | ............ 378/4 |
| 5,640,462 A | 6/1997 | Sato et al. | |
| 6,647,085 B2 | 11/2003 | Numata et al. | |
| 6,654,441 B2 | 11/2003 | Numata et al. | |
| 6,668,035 B2 | 12/2003 | Han et al. | |
| 6,778,681 B2 * | 8/2004 | Garms et al. | ............ 382/100 |
| 6,853,700 B1 | 2/2005 | Numata et al. | |
| 6,901,352 B2 * | 5/2005 | Woods et al. | ............ 702/189 |
| 2003/0099330 A1 * | 5/2003 | Mery et al. | ............ 378/210 |

FOREIGN PATENT DOCUMENTS

| | | |
|---|---|---|
| JP | 50-76526 A | 3/1993 |
| JP | 7-012759 A | 1/1995 |
| JP | 2003-530546 A | 10/2003 |
| JP | 2004-012407 A | 1/2004 |
| JP | 2004-034144 A | 2/2004 |

OTHER PUBLICATIONS

Japanese Office Action dated Sep. 29, 2009, issued in corresponding Japanese Patent Application No. 2004-313483.

* cited by examiner

*Primary Examiner* — Jon Chang
(74) *Attorney, Agent, or Firm* — Antonelli, Terry, Stout & Kraus, LLP.

(57) ABSTRACT

It is made possible to conduct inner defect inspection using spatial discrete data such as X-ray CT data with higher precision. An inner defect inspection method for inspecting inner defects in an object on the basis of spatial discrete data which describe spatial shape and structure of the object by using spatial elements includes the steps of: extracting an inner defect from the spatial discrete data by using an inner defect extraction unit, collecting the elements included in a neighborhood range, which is set with a predetermined spread around the inner defect extracted by the inner defect extraction unit, as related elements by using a related element collection unit; and measuring feature quantities such as a size and a position of center of gravity of the inner defect on the basis of the related elements collected by the related element collection unit, by using a feature quantity measurement unit.

5 Claims, 8 Drawing Sheets

METHOD OF INSPECTION FOR INNER DEFECTS OF AN OBJECT AND APPARATUS FOR SAME

BACKGROUND OF THE INVENTION

The present invention relates to a technique for inspecting cavity-like inner defects such as casting defects in casting parts. In particular, the present invention relates to a technique for inspecting an inner defect on the basis of spatial discrete data such as X-ray CT (Computed Tomography) data obtained by picking up an image of an object by using an X-ray CT apparatus.

In industrial products, a small cavity is generated inside a solid portion and becomes an inner defect that degrades the product performance in some cases. As a representative example of such an inner defect, there is a casting defect in a casting part. There is a possibility that the casting defect will exert a bad influence upon the strength or the like of the casting part. Therefore, a measure of decreasing occurrences of casting defects by adjusting the casting condition and controlling the occurrence position of casting defects by changing the shape of the runner of the die is adopted. Typically, in these measures, trial production and inspection are repeated at the stage of design and an optimum condition is searched for and determined. In the manufacturing field of casting parts, therefore, it becomes important to make it possible to inspect even a minimum casting defect with high precision.

As a technique for inspecting inner defects such as casting defects, there is a destructive inspection from old. In the destructive inspection, the inspection object is cut and its section is observed, or a cut piece obtained by cutting the object into dies is weighed. Such a destructive inspection requires labor and time, and the precision is not very high. In addition, it becomes impossible to conduct other tests such as a strength test on the object subjected to the destructive inspection, and the influence of inner defects upon the performance cannot be evaluated accurately.

On the other hand, nondestructive inspection of inner defects using an X-ray CT apparatus has become to be used in recent years. For example, in a system proposed in JP-A-7-12759, imaging of an inner section of a casting part is conducted using an X-ray CT apparatus and an inspection for inner defects is conducted. For example, in a system proposed in JP-A-2004-34144, a three-dimensional shape model of an object is generated from a plurality of sectional images picked up by an X-ray CT apparatus, and portions corresponding to inner defects in the three-dimensional shape model are colored to visually verify the inner defects. As for the inspection for casting defects, examples disclosed in JP-A-2004-12407 and JP-A-2003-530546 are also known.

The conventional techniques concerning the nondestructive inspection described above have merits that it is easy to visually grasp whether inner defects are present and positions of the inner defects. Especially in the method proposed in JP-A-2004-34144, three-dimensional distribution of inner defects can be grasped, resulting in a merit of reduced inspection labor and time.

In the method proposed in JP-A-2004-34144, however, it is necessary to generate a three-dimensional shape model of an object, resulting in a remained problem concerning the inspection precision and so on. For modeling an external shape of the object, a middle value between a CT value indicating a density of an inner defect portion (which is typically a density of air) and a CT value indicating a density of a solid portion is used as a threshold for modeling. Typically, in a sectional image obtained by an X-ray CT apparatus, however, a phenomenon that a boundary between an inner defect portion of a cavity structure such as a casting defect and a solid portion blurs, i.e., "blur" appears. In an inner defect of a minute cavity structure such as a casting defect in a casting part, therefore, a CT value of the defect portion (corresponding to a density of the defect portion) indicates a value shifted from an original CT value toward a CT value of a solid portion (corresponding to a density of the solid portion). In modeling using the threshold, such "blur" causes the size of the inner defect to become smaller than the actual size, or causes an inner defect having a size smaller than a definite size to become impossible in modeling itself, resulting in an insufficient inspection precision. If the threshold is made high so as to model even an inner defect having a small size, the volume of the inner defect differs according to the threshold, also resulting in lowered inspection precision. Furthermore, for modeling an inner defect with an accurate volume, it is necessary to make the threshold differ according to the size of the inner defect. As a result, the processing process of the inspection becomes complicated, and the inspection efficiency becomes lower.

In the context of the circumstances heretofore described, the present invention has been made.

A first object of the present invention is to provide an inner defect inspection method that makes it possible to conduct inner defect inspection using spatial discrete data such as X-ray CT data with higher precision and a higher efficiency.

A second object of the present invention is to provide an inner defect inspection apparatus that makes it possible to conduct inner defect inspection using spatial discrete data such as X-ray CT data with higher precision and a higher efficiency.

In order to achieve the first object in an inner defect inspection method for inspecting inner defects in an object on the basis of spatial discrete data which describe spatial shape and structure of the object by using spatial elements, the inner defect inspection method according to the present invention includes the steps of: extracting an inner defect from the spatial discrete data by using an inner defect extraction unit; collecting the elements included in a neighborhood range, which is set with a predetermined spread around the inner defect extracted by the inner defect extraction unit, as related elements by using a related element collection unit; and measuring feature quantities such as a size and a position of center of gravity of the inner defect on the basis of the related elements collected by the related element collection unit, by using a feature quantity measurement unit.

In order to achieve the first object in an inner defect inspection method for inspecting inner defects in an object on the basis of spatial discrete data which describe spatial shape and structure of the object by using spatial elements, the inner defect inspection method according to the present invention includes the steps of: measuring densities in the object on the basis of the spatial discrete data, finding density distribution, detecting an inner defect from the found density distribution, and setting a related region having a spread around a density measurement object region by using a region division setting unit; collecting the elements included in the related region set by the region division setting unit, from the spatial discrete data as related elements by using a related element collection unit; and measuring densities on the basis of the related elements collected by the related element collection unit, by using a density measurement unit.

In the inner defect inspection method according to the present invention, X-ray CT data is used as the spatial discrete data.

In order to achieve the second object, in an inner defect inspection apparatus for inspecting inner defects in an object on the basis of spatial discrete data which describe spatial shape and structure of the object by using spatial elements, the inner defect inspection apparatus according to the present invention includes: an inner defect extraction unit for extracting an inner defect from the spatial discrete data; a related element collection unit for collecting the elements included in a neighborhood range, which is set with a predetermined spread around the inner defect extracted by the inner defect extraction unit, as related elements; and a feature quantity measurement unit for measuring feature quantities such as a size and a position of center of gravity of the inner defect on the basis of the related elements collected by the related element collection unit.

In order to achieve the second object, in an inner defect inspection apparatus for inspecting inner defects in an object on the basis of spatial discrete data which describe spatial shape and structure of the object by using spatial elements, the inner defect inspection apparatus according to the present invention includes: a region division setting unit for measuring densities in the object on the basis of the spatial discrete data, finding density distribution, detecting an inner defect from the found density distribution, and setting a related region having a spread around a density measurement object region; a related element collection unit for collecting the elements included in the related region set by the region division setting unit, from the spatial discrete data as related elements; and a density measurement unit for measuring densities on the basis of the related elements collected by the related element collection unit.

In the inner defect inspection method according to the present invention, X-ray CT data is used as the spatial discrete data.

In accordance with the present invention, elements included in a neighborhood range, which is set with a predetermined spread around an inner defect are collected as related elements, and feature quantities of the inner defect are measured on the basis of the collected related elements. According to the present invention, therefore, it becomes possible to measure the feature quantities of the inner defects with high precision, resulting in raised inspection precision of the inner defects. It also becomes to conduct a series of processing automatically, resulting in highly efficient inspection.

In accordance with the present invention, densities in the object are measured on the basis of the spatial discrete data to find density distribution, and an inner defect is detected from the found density distribution. Elements included in a related region having a spread set around a density measurement object region are collected as related elements, and densities are measured on the basis of the related elements. According to the present invention, therefore, it is possible to efficiently detect inner defects such as microporosities formed by a large number of minute casting defects, each having a size of micrometer level, in a lump, resulting in raised inspection precision of the inner defects. It also becomes to conduct a series of processing automatically, resulting in highly efficient inspection.

Other objects, features and advantages of the invention will become apparent from the following description of the embodiments of the invention taken in conjunction with the accompanying drawings.

DESCRIPTION OF THE EMBODIMENTS

Hereafter, embodiments of the present invention will be described. In all embodiments described hereafter, the inner defect inspection apparatus is formed as an inner defect inspection apparatus that has a casting part as its object and that inspects casting defects as inner defects.

Figure 1:
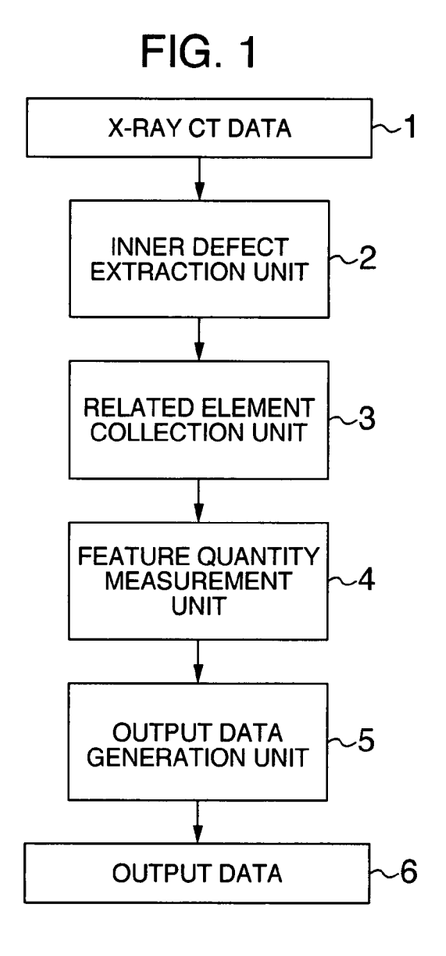
FIG. 1 is a diagram schematically showing a configuration in a processing function of an inner defect inspection apparatus according to a first embodiment.

FIG. 1 schematically shows a configuration in a processing function of an inner defect inspection apparatus according to a first embodiment. The inner defect inspection apparatus according to the present embodiment is formed by mounting an inner defect extraction unit 2, a related element collection unit 3, a feature quantity measurement unit 4 and an output generation unit 5, which are software elements, on a hardware element, such as a computer, which is not illustrated.

The inner defect extraction unit 2 extracts an inner defect, specifically a presence region of the inner defect from X-ray CT data 1 input as spatial discrete data. The related element collection unit 3 collects data (cell value or CT value) for each of elements contained in a region of an inner defect extracted by the inner defect extraction unit 2 and elements in a related range required to measure feature quantities (such as the size and the position of the center of gravity). The feature quantity measurement unit 4 measures feature quantities of an inner defect on the basis of data collected by the related element collection unit 3. The output generation unit 5 generates output data 6 on the basis of a result of the measurement conducted by the feature quantity measurement unit 4, and outputs the output data 6.

Here, the spatial discrete data is data describing a spatial shape and a spatial structure of an object by using spatial discrete elements. Representative one of the spatial discrete data is X-ray CT data. Elements of X-ray CT data are called "cells." The X-ray CT data is two-dimensional or three-dimensional bit map data of a data form having a spatial discrete arrangement of the cells. Each of the cells in the X-ray CT data has a value corresponding to a density in a corresponding portion of the object, and its value is typically called "cell value" or "CT value."

Figure 2:
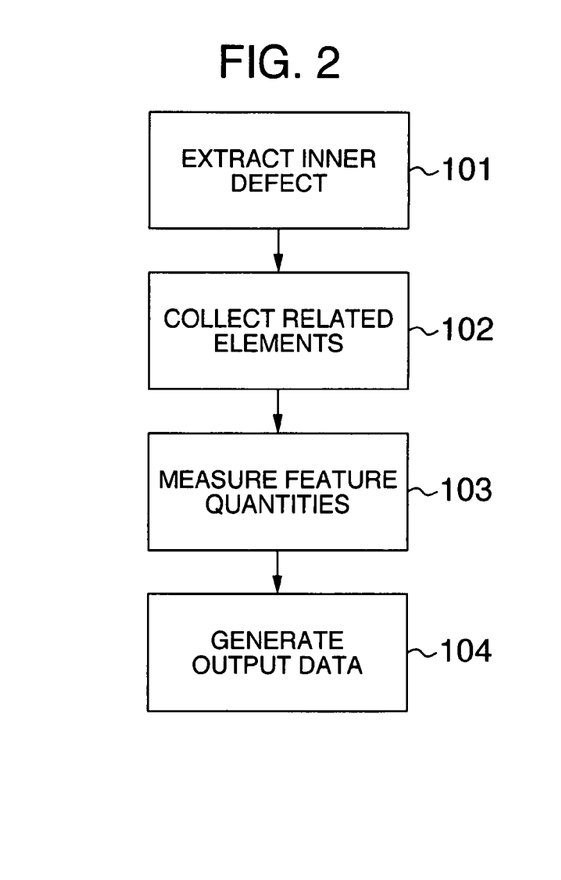
FIG. 2 is a diagram showing a flow of processing in the inner defect inspection apparatus shown in FIG. 1.
Figure 3:
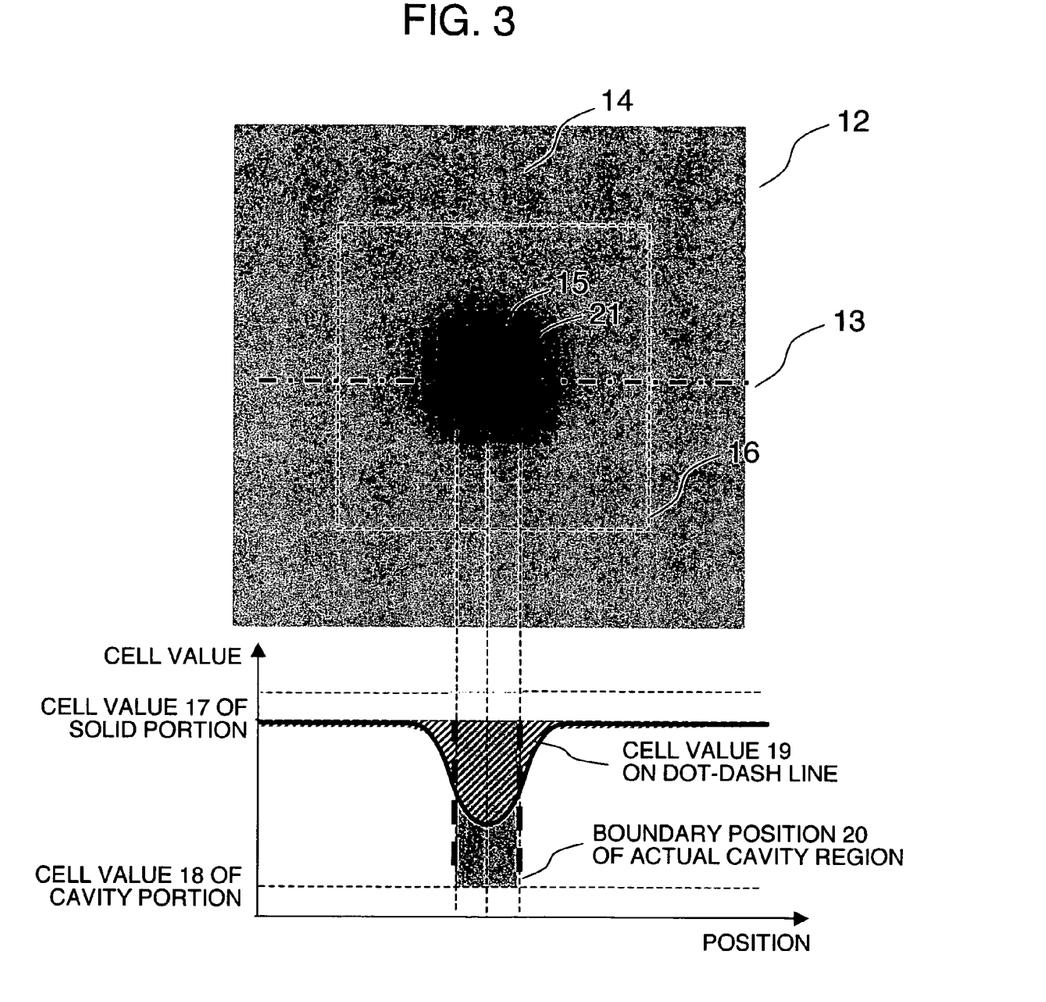
FIG. 3 is a diagram showing contents of processing ranging from extraction of an inner defect region to feature quantity measurement of the inner defect region, by using images.

Hereafter, contents of inspection processing conducted in the inner defect inspection apparatus will be described in more detail. FIG. 2 shows a flow of inspection processing. FIG. 3 shows contents of processing ranging from extraction of an inner defect region to feature quantity measurement of the inner defect region, by using images. In FIG. 3, an image (which is also referred to as X-ray CT data hereafter for convenience) 12 according to the X-ray CT data 6 containing an inner defect region is shown in an upper portion. A cell value of a cell located on a dot-dash line 13 is indicated by a graph shown in a lower portion of FIG. 3. The X-ray CT data 12 indicates a state in which an inner defect 15, which is a cavity originally represented by a black color, exists in a solid portion 14 represented by a light gray color. Supposing that the inner defect 15 has a spherical shape, the shape of the inner defect 15 is shown in FIG. 3. In general, however, each inner defect has anisotropy in its shape. Since the X-ray CT data 12 contains the above-described "blur," the inner defect 15 does not become perfect black, but becomes dark gray color. In the periphery of the inner defect 15, there is a portion having an intermediate color between the light gray color of the solid portion 14 and the dark gray color of the inner defect 15. In the graph, the abscissa indicates the position and the ordinate indicates the cell value. The graph represents a state in which the cell value on the dot-dash line 13 (indicated by a thick solid line 19) is distributed between a cell value of the solid portion represented by a thin dotted line 17 and a cell value of a region of the inner defect 15 represented by a thin dash line 18 (which is a cell value of the air when the inner defect is a cavity). This distribution is brought about by the "blur," and it becomes Gaussian distribution.

In the inspection processing, first, extraction of an inner defect 15 is conducted by the inner defect extraction unit 2 (step 101). There are two possible techniques for the processing conducted by the inner defect extraction unit 2 to extract the inner defect 15. In one of the techniques, a preset threshold for the inner defect extraction is supplied to the inner defect extraction unit 2. With respect to an inner defect 15 that is a cavity, the inner defect extraction threshold is set on the basis of the CT value of the air. The inner defect extraction unit 2 extracts the inner defect 15 from the X-ray CT data 6 by using the inner defect extraction threshold. In other words, the inner defect extraction unit 2 searches the X-ray CT data for cells each having a cell value that is equal to or less than the inner defect extraction threshold, extracts such cells, and identifies a region having such cells in a lump as the inner defect 15. In the other of the techniques, the inner defect extraction unit 2 suitably selects at least one cell on the X-ray CT data 6 as a reference cell, searches the neighborhood of the reference cell for cells each having a cell value that is different from a cell value of the reference cell by at least a definite value, extracts such cells, and thereby identifies the inner defect 15.

If the inner defect 15 is extracted as heretofore described, then the related element collection unit 3 conducts collection of related elements, i.e., collection of CT values concerning the related elements (step 102). Here, the term "related elements" means cells included in the region of the inner defect 15 extracted by the inner defect extraction unit 2 and cells included in a definite range around the inner defect 15, i.e., a neighborhood range 16 surrounded by a dash line in FIG. 3. The reason why CT values are collected for the cells included in the neighborhood range 16 as well will now be described. Because of the influence of the "blur," each of cells included in the inner defect 15 does not exhibit a cell value that the cell should originally have, but exhibits a cell value shifted to cell values that the cells in the solid portion 14 around the inner defect 15 have. If the cell value is used as it is, correct measurement of feature quantities can not be conducted. On the other hand, it becomes possible to measure the feature quantities of the inner defect 15 with high precision by collecting and using CT values of the cells in the neighborhood range as well.

The spread of the neighborhood range 16 is set according to the rough size of the inner defect 15. Typically, the neighborhood range 16 is set so as to include as many cells as, for example, approximately twice to three times the number of cells included in the inner defect 15, around the inner defect 15 nearly evenly. The shape of the neighborhood range 16 is set so as to nearly resemble the rough shape of the inner defect 15.

If the collection of the related elements is finished, then the feature quantity measurement unit 4 measures feature quantities of the inner defect 15 (step 103). The measurement of the feature quantities can be conducted utilizing the principle in "blur," such as a principle that "blur" can be represented by a Gaussian function. The size of the inner defect 15, which is one of the feature quantities, can be found as the volume of the inner defect 15 according to the following equation.

Volume of inner defect=(cell value of solid portion× the number of all collected cells−sum total of cell values of all collected cells)/(cell value of solid portion−cell value of inner defect region)

The position of the center of gravity 21 of the inner defect 15, i.e., the position of the inner defect 15, which is one of the feature quantities, can be found using a technique of, for example, weighting the cells. In addition, feature quantities such as the principal axis of the inertia moment of the inner defect 15 and the length of the inner defect 15 in the lengthwise direction can also be found on the basis of positions and cell values of collected cells. By thus using cell values of collected related elements for the neighborhood range as well, it becomes possible to measure the feature quantities with high precision even for a minute inner defect having a size that is equal to or less than a size of blur range.

If the measurement of the feature quantities is finished, then the output data generation unit 5 generates the output data 6 on the basis of the result of the measurement conducted by the feature quantity measurement unit 4, and outputs the output data 6 (step 104). The output data 6 is generated as data that can display the measured result on a display in a state in which the user can visually distinguish with ease or data that can be statistically rearranged with ease.

Figure 4:
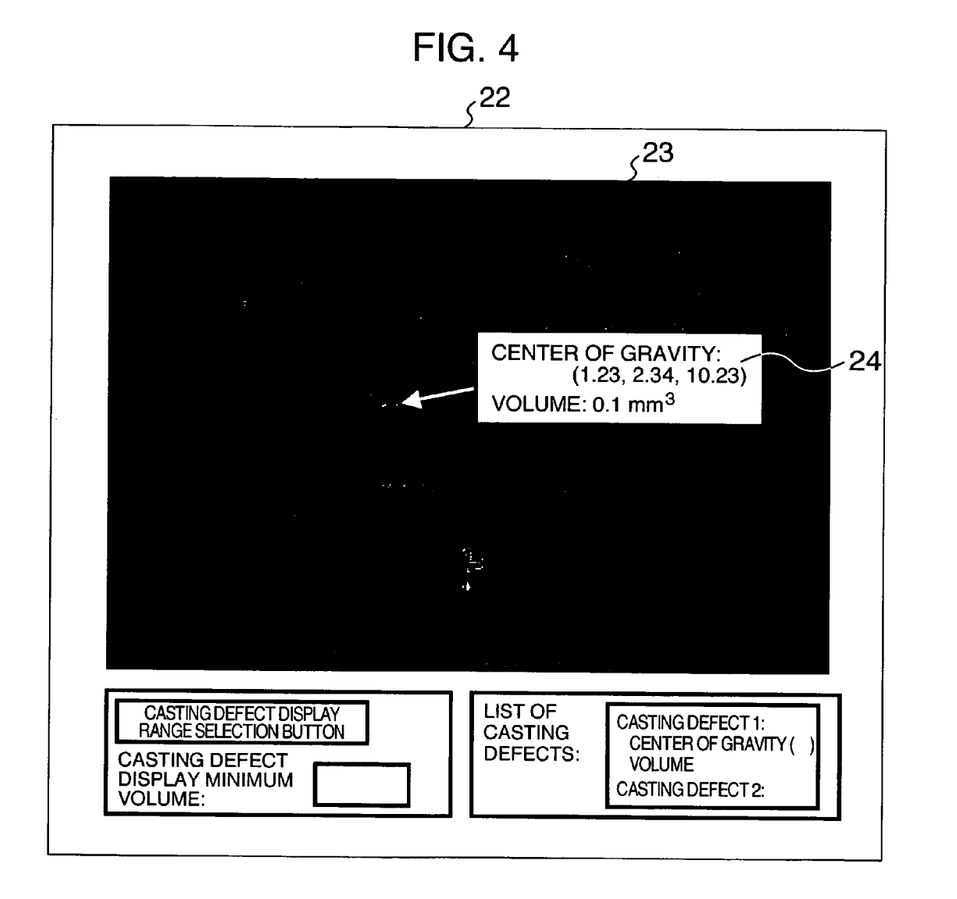
FIG. 4 is a diagram showing a display example of output data in the inner defect inspection apparatus shown in FIG. 1.

FIG. 4 shows an example of output data displayed on the display. An image 23 based on the X-ray CT data (three-dimensional or two-dimensional bit map data) is displayed on a screen 22 of the display. In the case of the three-dimensional bit map data, the image 23 is typically a rendering image. In the case of the two-dimensional bit map data, the image 23 becomes a sectional image. The image 23 displays the external shape and the inner defect of the object simultaneously. As for the display of the inner defect, it is desirable to conduct enhancement display by conducting color distinction display or expansion display according to the feature quantities. Furthermore, it is also desirable to display only inner defects in the range selected by the user or display only inner defects having at least a size selected by the user. It is also a favorable example to display an indicator 24 by superposing the indicator 24 on the image 23 and display the feature quantities of the inner defect quantitatively on the indicator 24. In this case, it is desirable to quantitatively display the feature quantities in an inner defect arbitrarily selected by the user, on the indicator 24 by aligning the indicator 24 to the position of the inner defect.

For displaying an inner defect, it is necessary to extract data of an inner defect region from X-ray CT data including the external shape of the object (contour of the object). The extraction processing can be conducted as hereafter described. First, enhancement display of an air portion is conducted by, for example, inverting cell values of all cells in the original X-ray CT data. Subsequently, an air portion (a cell portion having the cell value of the air) outside the external shape of the object is searched for by using the well-known region growing technique, and deleted. By doing so, the emphasized portions become only inner defects and data of the inner defects can be extracted. If one-bit three-dimensional bit map data for reference is utilized at this time, it can be used as an index and faster processing can be implemented. Furthermore, it is also possible to extract only inner defects in the vicinity of the boundary between the object and the outside air, by bringing a threshold for region growing close to the cell value of the solid portion at the time of region growing of the outside air portion. This can be achieved by conducting set operation of design data of external shape such as CAD data and the outside air portion subjected to region growing.

Figure 5:
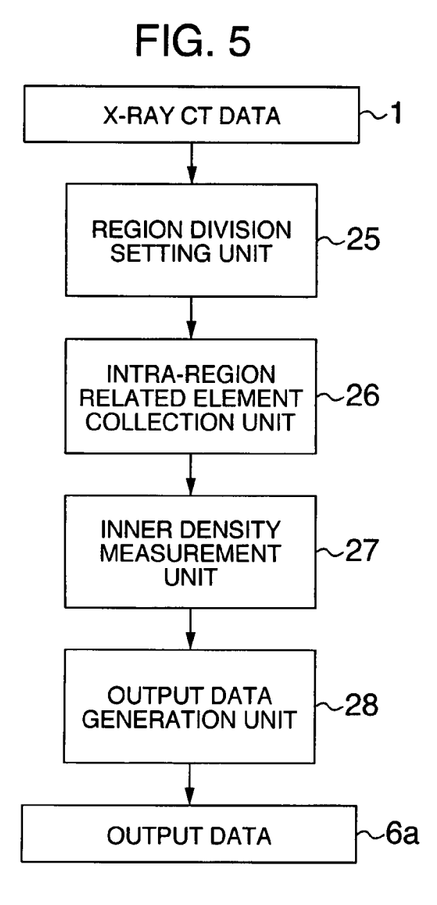
FIG. 5 is a diagram schematically showing a configuration in a processing function of an inner defect inspection apparatus according to a second embodiment.

FIG. 5 schematically shows a configuration in a processing function of an inner defect inspection apparatus according to a second embodiment. The inner defect inspection apparatus according to the present embodiment is formed so as to be suitable for detecting inner defects such as microporosities or porous defects formed by a large number of minute casting defects, each having a size of micrometer level, in a lump. The basis idea in detection of inner defects such as microporosities is to measure the density with respect to the X-ray CT data of the object, find the density distribution, and detect inner defects on the basis of the density distribution. In other words, if there is a portion having a density that is less than the density in the neighborhood by at least a definite value, the portion is detected as an inner defect. Therefore, the inner defect inspection apparatus is formed by mounting a region division setting unit 25, a related element collection unit 26, a density measurement unit 27 and an output data generation unit 28 on a hardware element such as a computer, which is not illustrated.

Figure 6:
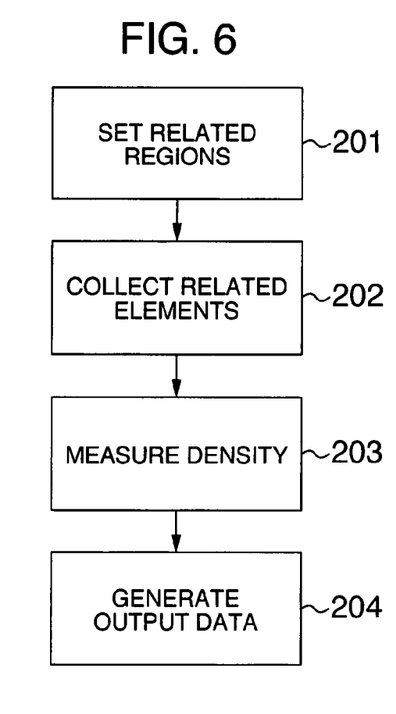
FIG. 6 is a diagram showing a flow of processing in the inner defect inspection apparatus shown in FIG. 5.

FIG. 6 shows a flow of inspection processing. First, the region division setting unit 25 sets related regions with respect to an object included in input X-ray CT data 1 (step 201). Related regions are regions each having a predetermined spread around a density measurement object region, and they are set by dividing the object in shape. The division of the object is conducted by, for example, dividing the object into grids (dies in the case of three-dimensional bit map data). In the case where the object is divided into grids having even sizes, it suffices to specify the size of the grids. The sizes of the grids may not be even, and in that case sizes respectively of grids are specified. Division of the object may be conducted for the whole object, or may be conducted only for a specific portion.

If the related regions are set, then the related element collection unit 26 conducts collection of related elements, i.e., conducts collection of CT values of the related elements (step 202). Here, related elements in the case of density measurement are cells included in a range required to find the density of the density measurement object region as an average density which can exclude the influence of noise in the X-ray CT data. The reason why collection of such related elements is conducted will be described hereafter. Noise in the X-ray CT data occurs at random every cell. With respect to a suitable spread range around the density measurement object region, therefore, an average value of cell values of cells included in the range is found. The average value is used as a representative cell value, i.e., a representative density value in the density measurement object region. As a result, it is possible to cancel the influence of noise generated at random every cell and reduce the influence of noise. Therefore, it becomes possible to remarkably raise the precision of the density measurement. For such a reason, there is a suitable size for the related regions. In one example, the size of the density analysis object region is set equal to 2×2=4 cells or 3×3=9 cells (where the size of each cell is, for example, approximately 200μ), and a related region is set so as to include several hundreds to several thousands cells around and next to the density analysis object region. Basically, related elements are cells in each related region. As occasion demands, however, cells in the vicinity of the related region are included in some cases.

Figure 7:
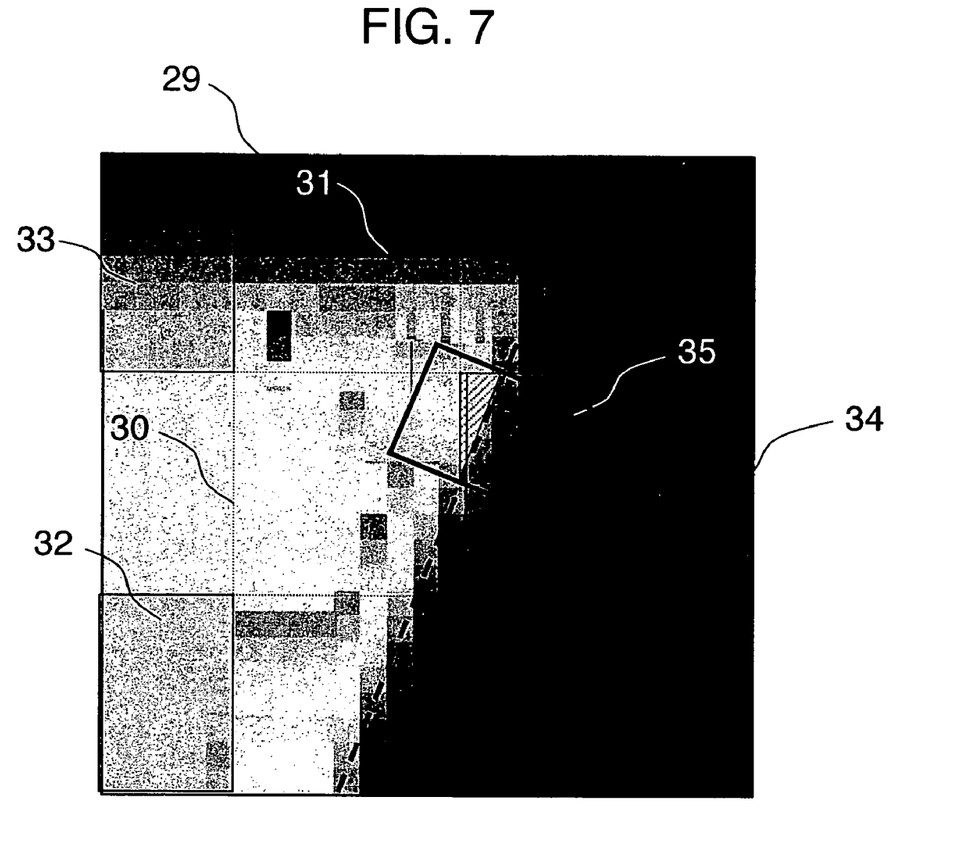
FIG. 7 is a diagram showing contents of density measurement processing by using an image.

If collection of the related elements is finished, then the density measurement unit 27 measures the density (step 203). FIG. 7 shows contents of density measurement processing by using an image. Although FIG. 7 shows a two-dimensional example, the principle is the same in the three-dimensional case as well. In X-ray CT data 29, a cell value of each cell corresponds to a density of a region corresponding to the cell in the object. The X-ray CT data 29 indicates that there is a certain object indicated by the gray color in the air indicated by the black color. A dotted line 30 indicates a boundary of a related region. A thick dash line 31 indicates a boundary between the object and the air (object/air boundary). This boundary can be automatically distinguished using a threshold for boundary detection. It is also possible to find the boundary by referring to CAD data. Among related regions, there is a region like a region (related region) 32 that is wholly located sufficiently inside from the boundary, i.e., that is inside the object enough to be free from the influence of the "blur" at the boundary. Among the related regions, there is a region like a region 33 or a region 34 that is in close vicinity to the boundary or includes the boundary.

In the case of the related region 32 that is wholly located sufficiently inside the object, an average density is found as an average value of cell values of all cells included in the related region 32. The region 33 located near the boundary includes cells located outside the boundary, i.e., cells in the air portion as well. Therefore, a cell value indicating the density of the air is previously found, and the average density is found using the following equation.

Average density=(sum total of cell values of all cells inside and outside boundary−cell value indicating density of air×volume outside boundary in region)/(volume inside boundary in region)

In the same way as the region 33, the region 34 includes cells located outside the boundary as well. In the same way as the region 33, therefore, an average density is found. In the region 34, however, a cell in an object portion is located at a corner portion of the region. In such a case, cells outside the region are also collected as related elements. In the example shown in FIG. 7, an auxiliary region 35 is set and related elements are collected in the auxiliary region 35 as well. Thus, it is possible to find the density distribution of the object with high precision even near the boundary regardless of the way of region division or the shape of the object. As for a region having a density that differs from a definite range, regions that further divide the region may be set and measurement may be conducted again. By doing so, it becomes possible to further raise the measurement precision.

If the density measurement is finished, the output data generation unit 28 generates output data 6a on the basis of a result of the density measurement conducted by the density measurement unit 27, and outputs the output data 6a (step 204). The output data 6a is typically data identifying a region of an inner defect such as a microporosity. However, the output data 6a may be density distribution data. In the case where density distribution data is used as the output data 6a, it is generated as data capable of displaying the measurement result on the display in a state in which the measurement result is visually seen with ease, or data that facilitate rearrangement of the regions and densities in the regions. In the case where a visual output is used, it is desirable to display only regions that have at least a definite value in density or only regions that have at most a definite value in density, with enhancement or display regions with colors according to densities. It is also desirable to provide only regions that have at least a definite value in density or only regions that have at most a definite value in density, with tags when outputting the output data 6a. Such density distribution data also make it possible to grasp inner defects.

Figure 8:
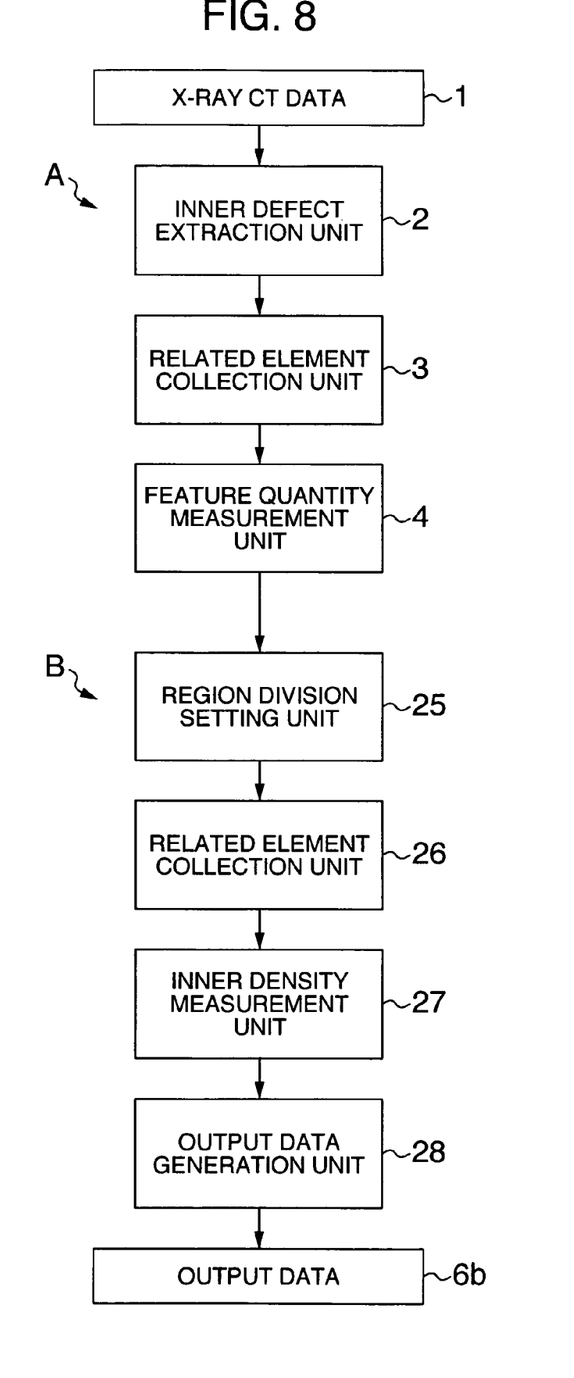
FIG. 8 is a diagram schematically showing a configuration in a processing function of an inner defect inspection apparatus according to a third embodiment.

FIG. 8 schematically shows a configuration in a processing function of an inner defect inspection apparatus according to a third embodiment. The inner defect inspection apparatus according to the present embodiment is formed to have both the function of the inner defect inspection apparatus according to the first embodiment and the function of the inner defect inspection apparatus according to the second embodiment. Specifically, the inner defect inspection apparatus according to the present embodiment includes a first defect inspection function unit A for conducting first inner defect inspection processing and a second defect inspection function unit B for conducting second inner defect inspection processing. In the same way as the inner defect inspection apparatus according to the first embodiment, the first defect inspection function unit A includes an inner defect extraction unit 2, a related element collection unit 3, and a feature quantity measurement unit 4 as software elements. On the other hand, in the same way as the inner defect inspection apparatus according to the second embodiment, the second defect inspection function unit B includes a region division setting unit 25, a related element collection unit 26, a density measurement unit 27 and an output data generation unit 28 as software elements. Since processing conducted by each of the first defect inspection function unit A and the second defect inspection function unit B is basically the same as that described above, its description will be omitted.

Hereafter, processing unique to the inner defect inspection apparatus having both the defect inspection function unit A and the defect inspection function unit B according to the present embodiment will be described. As described above, the defect inspection function unit B is suitable for detection of inner defects having a lump structure of minute casting defects such as microporosities. In many cases, such inner defects are present around inner defects larger in size than casting defects that are in the order of micrometer in size. Therefore, the defect inspection function unit A first detects a large inner defect, and then the defect inspection function unit B detects an inner defect having a minute casting defect lump structure around the large inner defect. By doing so, the precision and efficiency can be raised in detection of inner defects each having a minute casting defect lump structure. Furthermore, since the defect inspection function unit A finds feature quantities of inner defects each having a minute casting defect lump structure, it becomes possible to measure their total volume, center of gravity, and distribution area. Thus, it becomes possible to further raise the effectiveness of the defect inspection. By the way, in the present embodiment, the defect inspection function unit A is disposed in a preceding stage. Alternatively, the defect inspection function unit B may be disposed in the preceding stage.

Figure 9:
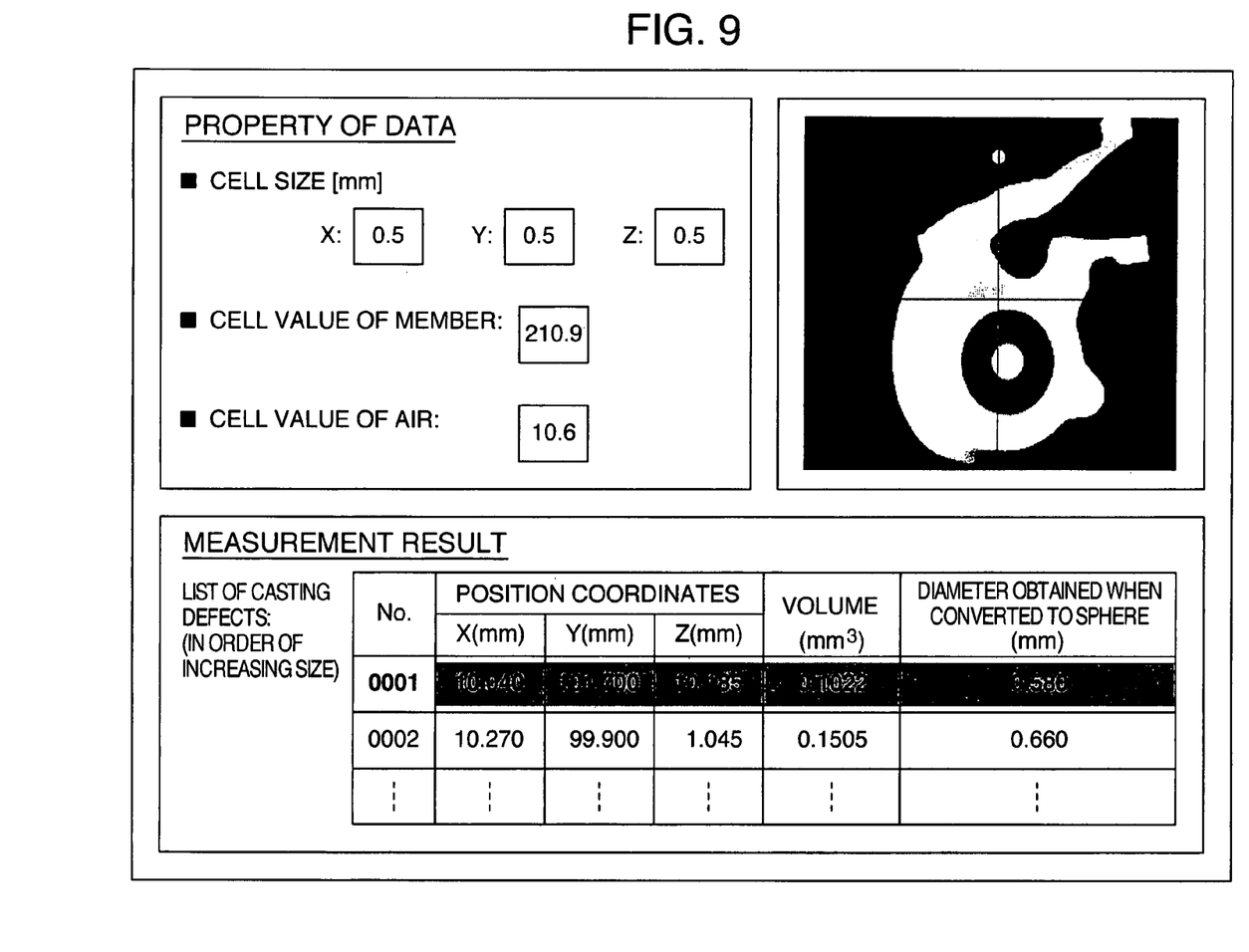
FIG. 9 is a diagram showing an example of implementing measurement of a minute casting defect and displaying the minute casting defect on a screen in the first or third embodiment.

Display of the inspection result will now be described with reference to FIG. 9. FIG. 9 is a diagram showing an example of implementing the measurement of minute casting defects and displaying a result of the measurement on a screen in the present embodiment. In this display screen, a view for inputting and displaying data properties, a view for displaying a list of measurement results, and a view for visually illustrating a measurement result. As a matter of fact, however, these views need not necessarily be displayed at the same time. Although the visual display view of the measurement result displays a two-dimensional section, display using a three-plane view or three-dimensional display may be used.

Here, defect data in the measurement results are separate from the shape data in the measurement dimension. The defect data can be displayed by changing the color or making the shape semi-transparent. The list display of the measurement results differs according to the data property setting values, and the measurement results can be rearranged in the order of position coordinate or in the order of volume. Furthermore, by selecting an arbitrary defect in the list, the position of the selected defect can also be displayed in the visual display view. Conversely, quantitative information of a defect selected in the visual display view can be known in the list.

For quantitatively indicating the size in the three-dimensional bit map data, it is necessary to set the size of a cell, which is the minimum unit. For example, in FIG. 9, the cell size is set equal to 0.5 mm×0.5 mm×0.5 mm. In the case where the present embodiment is not used, the resolution of data is restricted by the cell size. Since the resolution of data is one cell, the minimum casting defect volume in the measurement results becomes 0.125 mm$^3$. On the other hand, in the present embodiment, a casting defect having a size that is approximately equal to the voxel size can be detected, and consequently a casting defect having a minute volume 0.1022 mm$^3$ is also detected. In the case where the present invention is not utilized, the defect volume is indicated at intervals of 0.125 mm$^3$. In the present embodiment, however, a casting defect having a middle volume between 0.125 mm$^3$ and 0.25 mm$^3$ can be detected with high precision. In other words, in an inner defect display method for inspecting and displaying inner defects in an object on the basis of spatial discrete data which describe spatial shape and structure of the object by using spatial elements, an inner defect smaller in size than a cell, which is an element of the spatial discrete data, can be displayed and an inner defect smaller in size than a cell can be ascertained easily without being restricted by the cell size. Furthermore, an inner defect can be displayed with precision smaller than the cell size, and an inner defect can be ascertained easily with precision smaller than the cell size without being restricted by the cell size. The present embodiment is suitable especially for improving the detection precision and measurement precision for inner defects of casting parts. Furthermore, it is desirable to find feature quantities of an inner defect based on related elements included in a neighborhood range set with a predetermined spread around the inner defect, and display the inner defect.

Figure 10:
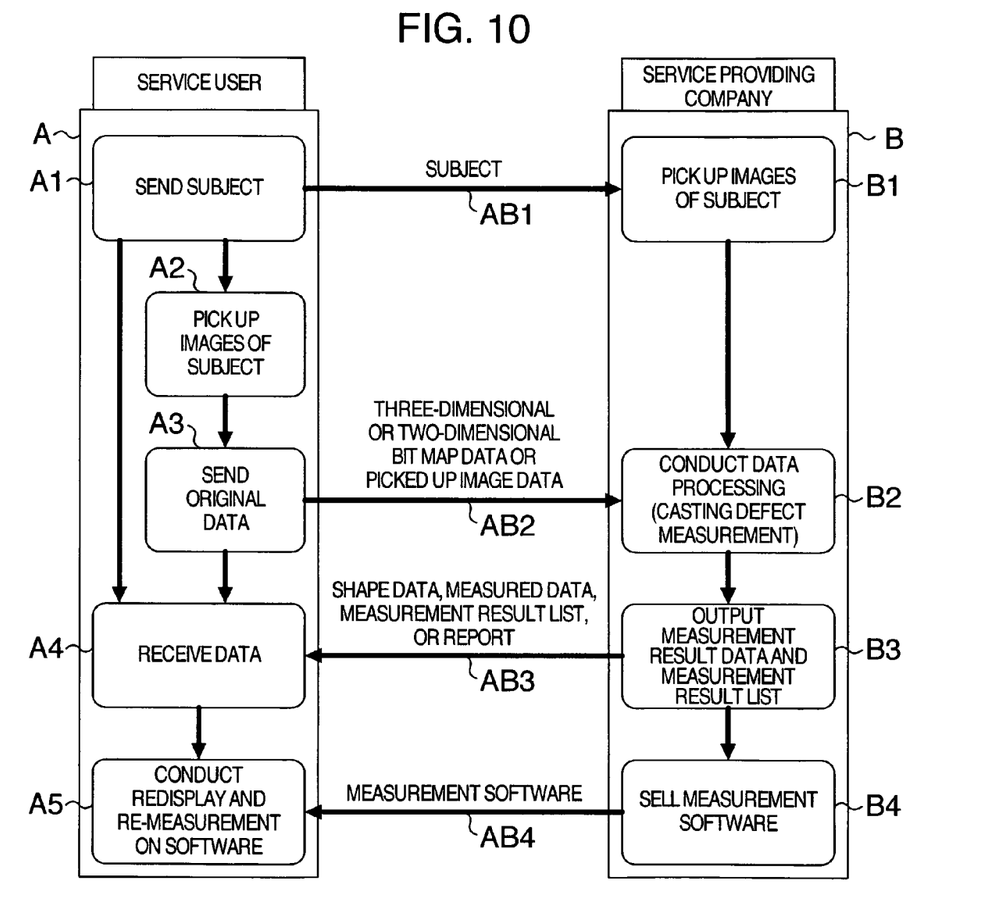
FIG. 10 is a diagram showing casting defect measurement providing service.

FIG. 10 is a diagram showing an example of an embodiment according to the present invention. As to service for providing casting defect measurement according to the present embodiment, a flow of procedure followed by a service user A is denoted by A1 to A5, and a flow of procedure followed by a service provider B is denoted by B1 to B4. A flow of objects delivered between them is denoted by AB1 to AB4. Data capable of displaying an inner defect in an object is output on the basis of spatial discrete data that describes the spatial shape and structure of the object by using spatial discrete elements.

First, the service user A sends a subject AB1, which is an object to be measured, to the service providing company B (A1). Upon receiving this, the service providing company B picks up images of the subject by using an X-ray CT apparatus or the like (B1), generates three-dimensional or two-dimensional bit map data on the basis of the picked up image data, and obtains spatial discrete data. The service providing company B conducts casting defect measurements (B2) on the data by using the method described with reference to FIG. 4, and outputs a result as three-dimensional or two-dimensional bit map data and list data (B3). The service user A receives shape data preceding the measurement and casting defect data obtained as a result of the measurement, in the form of three-dimensional or two-dimensional bit map data as a service outcome AB3. The service user A receives at least casting defect data. Furthermore, the service user A can receive list data of the measurement result as well, and receive sectional images and three-dimensional fluoroscopic images of main defects as well as a report (A4). Here, the service providing company B can output data capable of displaying inner defects with a size or precision smaller than the size of a cell, which is an element of the spatial discrete data. The service user A can obtain defect data of minute defects and defect data of high precision, and ascertain defects suitably. Furthermore, feature quantities of inner defects based on related elements included in a neighborhood range set with a predetermined spread around an inner defect may be found on the basis of data capable of displaying an inner defect.

As for the service utilization form of the service user A, the service user A can receive service without sending a subject, by picking up images of the subject by using an X-ray CT apparatus that the service user A has or an apparatus that another company has (A2) and sending resultant picked up image data or three-dimensional or two-dimensional bit map data (AB2) to the service providing company B as spatial discrete data (A3).

In addition, the service providing company may sell measurement software AB4 itself to the service user A4 (B4). As a result, the service user A can freely re-display the service outcome AB3 on the screen described with reference to FIG. 9, and output results of re-measurement. The service user can conduct measurement individually after the image pickup of the subject.

The present invention makes it possible to conduct inner defect inspection using spatial discrete data such as X-ray CT data, with higher precision. The present invention can be applied widely to fields such as inspection for casting defects of casting parts.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inner defect inspection method for inspecting inner defects in an object of casting parts on the basis of X-ray CT cell values obtained by imaging said object of casting parts by an X-ray CT apparatus, said X-ray CT cell values corresponding to density of said object, said inner defect inspection method comprising the steps of:
   extracting an inner defect from X-ray CT data of the object of casting parts by using inner defect extraction means;
   collecting a plurality of X-ray CT cells included in a neighborhood range, which is set with twice to three times the number of X-ray CT cells included in the inner defect around the inner defect extracted by the inner defect extraction means, as related X-ray CT cells by using related element collection means from the X-ray CT data of the object of casting parts;
   measuring feature quantities of the inner defect on the basis of the related elements collected by the related X-ray CT cells collection means, by using feature quantity measurement means; and
   displaying inner defects whose measured feature quantities satisfy a predetermined threshold on a display.

2. An inner defect inspection method for inspecting inner defects in an object of casting parts on the basis of X-ray CT cell values obtained by imaging said object of casting parts by an X-ray CT apparatus, said X-ray CT cell values corresponding to density of said object, said inner defect inspection method comprising the steps of:
   measuring densities in the object on the basis of X-ray CT data of the object of casting parts, finding density distribution, detecting an inner defect from the found density distribution, and setting a related region having a spread around a density measurement object region by using region division setting means;
   collecting a plurality of X-ray CT cells included in the related region set by the region division setting means, from the X-ray CT data of the object of casting parts as related X-ray cells by using related element collection means;
   measuring densities on the basis of the related X-ray CT cells collected by the related element collection means, by using density measurement means; and
   displaying inner defects whose measured densities satisfy a predetermined threshold on a display.

3. An inner defect display method for inspecting and displaying inner defects in an object of casting parts, comprising:
   obtaining X-ray CT cell values by imaging said object of casting parts by an X-ray CT apparatus,
   said X-ray CT cell values corresponding to density of said object,
   wherein feature quantities of the inner defect based on related X-ray CT cells included in a neighborhood range which is set with twice to three times the number of X-ray CT cells included in the inner defect around the inner defect are obtained, and an inner defect is displayed with a size or precision smaller than a size of the X-ray CT cells on a display.

4. An inner defect display method for outputting data capable of displaying inner defects in an object of casting parts, comprising:
   obtaining X-ray CT cell values by imaging said object of casting parts by an X-ray CT apparatus,
   said X-ray CT cell values corresponding to density of said object,
   wherein feature quantities of the inner defect based on related X-ray CT cells included in a neighborhood range which is set with twice to three times the number of cells included in the inner defect around the inner defect are obtained, and
   displaying the inner defect with a size or precision smaller than a size of the X-ray CT cells on a display.

5. An inner defect inspection method for inspecting inner defects in an object of casting parts on the basis of X-ray CT cell values obtained by imaging said object of casting parts by an X-ray CT apparatus, said X-ray CT cell values corresponding to density of said object, said inner defect inspection method comprising the steps of:
   extracting an inner defect from X-ray CT data of the object of casting parts by using inner defect extraction means;
   collecting a plurality of X-ray CT cells included in a neighborhood range which is set with twice to three times the number of X-ray CT cells included in the inner defect around the inner defect extracted by the inner defect extraction means, as related X-ray CT cells by using related element collection means from the X-ray CT data of the object of casting parts;

measuring a volume of the inner defect on the basis of an X-ray CT cell value of a solid portion of the object and an X-ray CT cell value of an inner defect region collected by the related element collection means, by using feature quantity measurement means; and displaying inner defects whose measured volumes satisfy a predetermined threshold on a display.

* * * * *